United States Patent
Cho et al.

(10) Patent No.: US 8,911,951 B2
(45) Date of Patent: Dec. 16, 2014

(54) PLASMA KALLIKREIN FRAGMENTS AS DIAGNOSTIC BIOMARKERS FOR LUNG CANCERS

(75) Inventors: Je-Yeol Cho, Daegu (KR); Jae-Yong Park, Daegu (KR); Seung-Jin Lee, Daegu (KR)

(73) Assignee: Protan Bio Co., Ltd., Daegu (KR)

( * ) Notice: Subject to any disclaimer, the term of this patent is extended or adjusted under 35 U.S.C. 154(b) by 0 days.

(21) Appl. No.: 13/494,215

(22) Filed: Jun. 12, 2012

(65) Prior Publication Data

US 2012/0252039 A1 Oct. 4, 2012

Related U.S. Application Data

(62) Division of application No. 12/531,564, filed as application No. PCT/KR2007/004322 on Sep. 6, 2007, now abandoned.

(30) Foreign Application Priority Data

Mar. 21, 2007 (KR) ........................ 10-2007-0027541

(51) Int. Cl.
*G01N 33/53* (2006.01)

(52) U.S. Cl.
USPC ......................................................... 435/7.1

(58) Field of Classification Search
None
See application file for complete search history.

(56) References Cited

U.S. PATENT DOCUMENTS 5,444,156 A * 8/1995 Veloso et al. ................. 435/337
2009/0136960 A1 * 5/2009 Lubman et al. .................. 435/6

FOREIGN PATENT DOCUMENTS

WO      2005/075665 A2 *  8/2005
WO   WO 2005/107491      * 11/2005

OTHER PUBLICATIONS

Kultima et al (BMC Bioinformatics, 2006, 7:475, internet pp. 1-27).*
Sambrook et al. (Molecular Cloning, 2nd edition, Cold Spring Harbor Press, 1989, p. 18.47).*
Invitrogen™ product information sheet for protein standards and ladders; printed 2008.*
Zhao et al (J of Proteome Research, 2007, 6:1126-1138, published online Jan. 24, 2007).*
Ping et al (Proteomics, 2005, 5:3506-3519).*
Tao Liu, et al; "Human Plasma N-Glycoproteome Analysis by Immunoaffinity Substraction, Hydrazide Chemistry, and Mass Spectrometry", J. Proteome Res. Web Publication Date: Oct. 26, 2005; vol. 4, Issue 6, pp. 2070-2080.
CM Maciel, et al; "Differential proteomic serum pattern of low molecular weight proteins expressed by adenocarcinoma lung cancer patients", 2005: vol. 5, Issue 1: pp. 31-38.
Tetsuya Okano, et al; "Plasma proteomics of lung cancer by a linkage of multi-dimensional liquid chromatography and two-dimensional difference gel electrophoresis", Proteomics; Jul. 2006; vol. 6, Issue 13; pp. 3938-3948.
D Maxwell Parkin; "Global cancer statistics in the year 2000", The Lancet Oncology, vol. 2, Sep. 2001, pp. 533-543.
Giulio Tarro, et al; "Early Diagnosis of Lung Cancer by Detection of Tumor Liberated Protein" Journal of Cellular Physiology; vol. 203, Issue 1, pp. 1-5; Apr. 2005.
Keith Vosseller, et al; "O-Linked N-Acetylglucosamine Proteomics of Postsynaptic Density Preparations Using Lectin Weak Affinity Chromatography and Mass Spectrometry", Molecular & Cellular Proteomics, vol. 5, pp. 923-934; First Published on Feb. 1, 2006; doi:10.1074/mcp.T500040-MCP200.
Z. Yang, et al; "Approach to the comprehensive analysis of glycoproteins isolated from human serum using a a multi-lectin affinity column", J. Chromatogr A; Oct. 22, 2004; vol. 1053(1-2) pp. 79-88.
Ziping Yang, et al; "A study of glycoproteins in human serum and plasma reference standards (HUPO) using multilectin affinity chromatography coupled with RPLC-MS/MS", Proteomics, Received Jul. 8, 2004; pp. 3353-3366.
Kenneth H. Yu, et al; "Characterization of Proteins in Human Pancreatic Cancer Serum Using Differential Gel Electrophoresis and Tandem Mass Spectrometry", Journal of Proteome Research; Received Jun. 11, 2005; vol. 4, pp. 1742-1751.
Hui Zhang, et al; "High Throughput Quantitative Analysis of Serum Proteins Using Glycopeptide Capture and Liquid Chromatography Mass Spectrometry", Molecular & Cellular Proteomics 4.2; Received Jul. 12, 2004, pp. 144-155; paper is available online at http://www.mcponline.org.

* cited by examiner

*Primary Examiner* — Laura B Goddard
(74) *Attorney, Agent, or Firm* — Ladas & Parry LLP

(57) ABSTRACT

Disclosed herein are diagnostic markers for lung cancer, isolated from serum glycoproteins. The disclosed diagnostic markers for lung cancer are specifically expressed only in the sera of lung cancer patients at high levels, and thus will be very useful for diagnosing lung cancer and estimating disease progression and treatment.

11 Claims, 6 Drawing Sheets

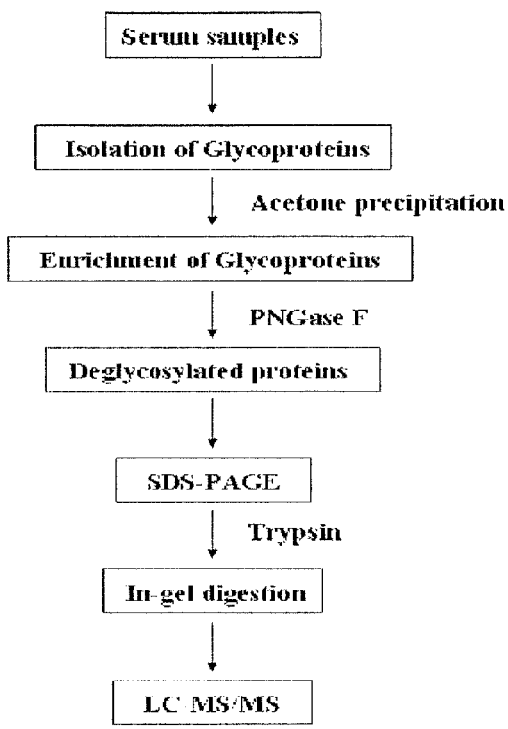
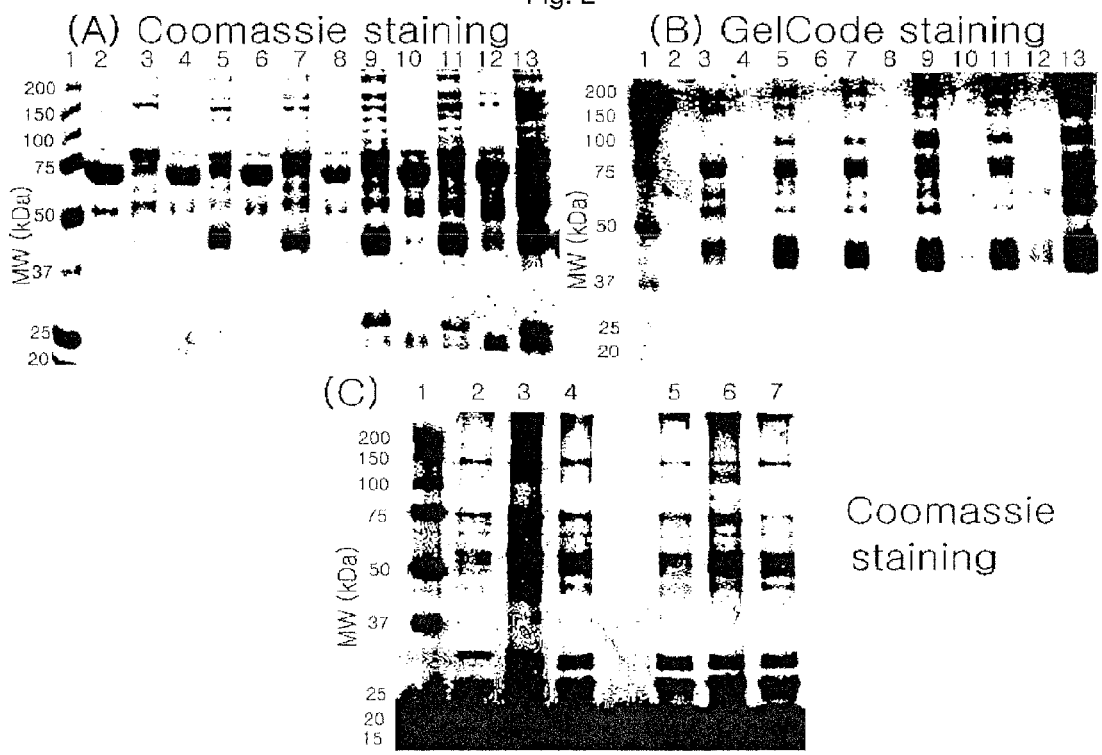

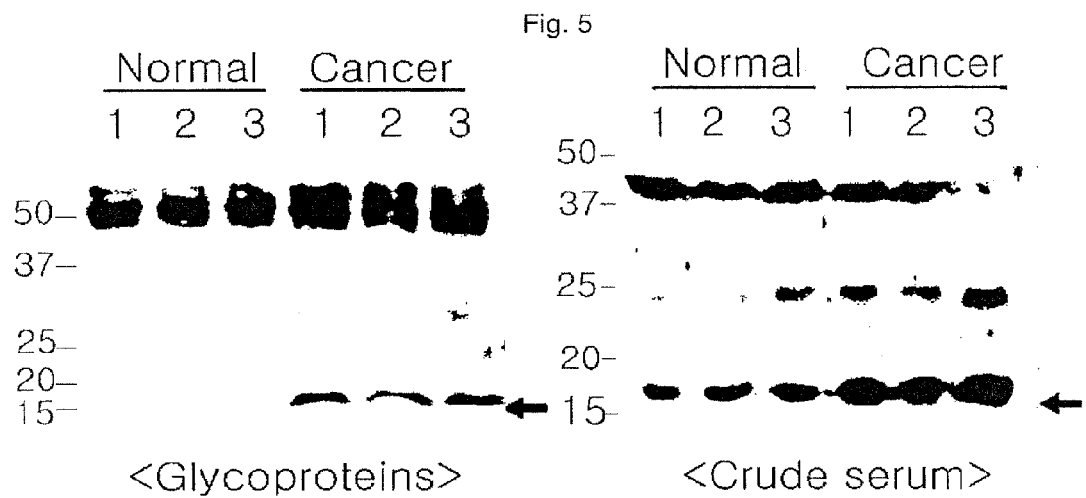
Fig. 5
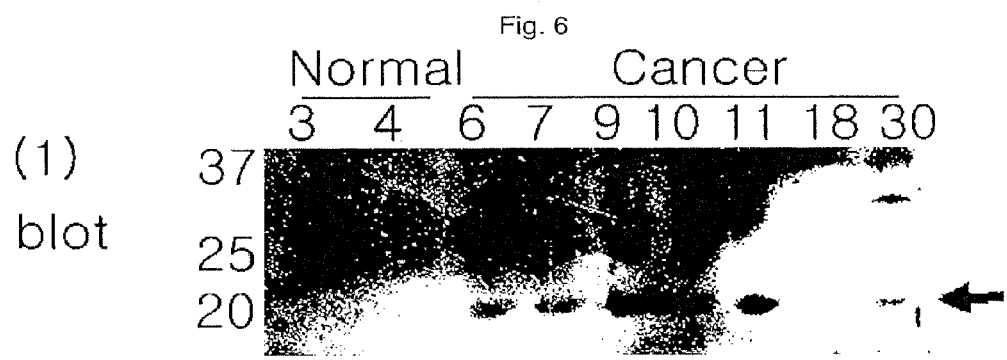
Fig. 6
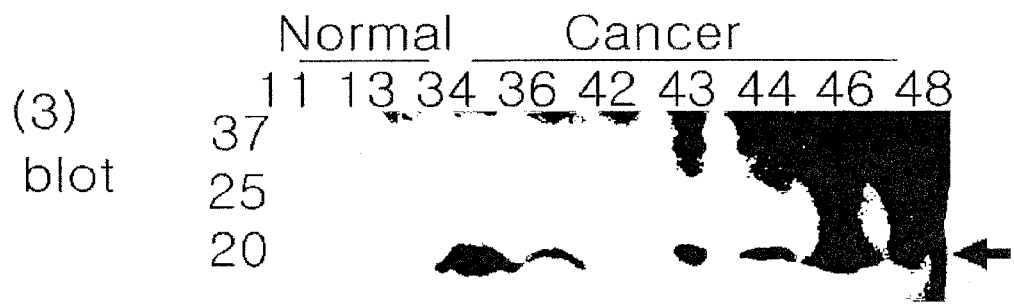

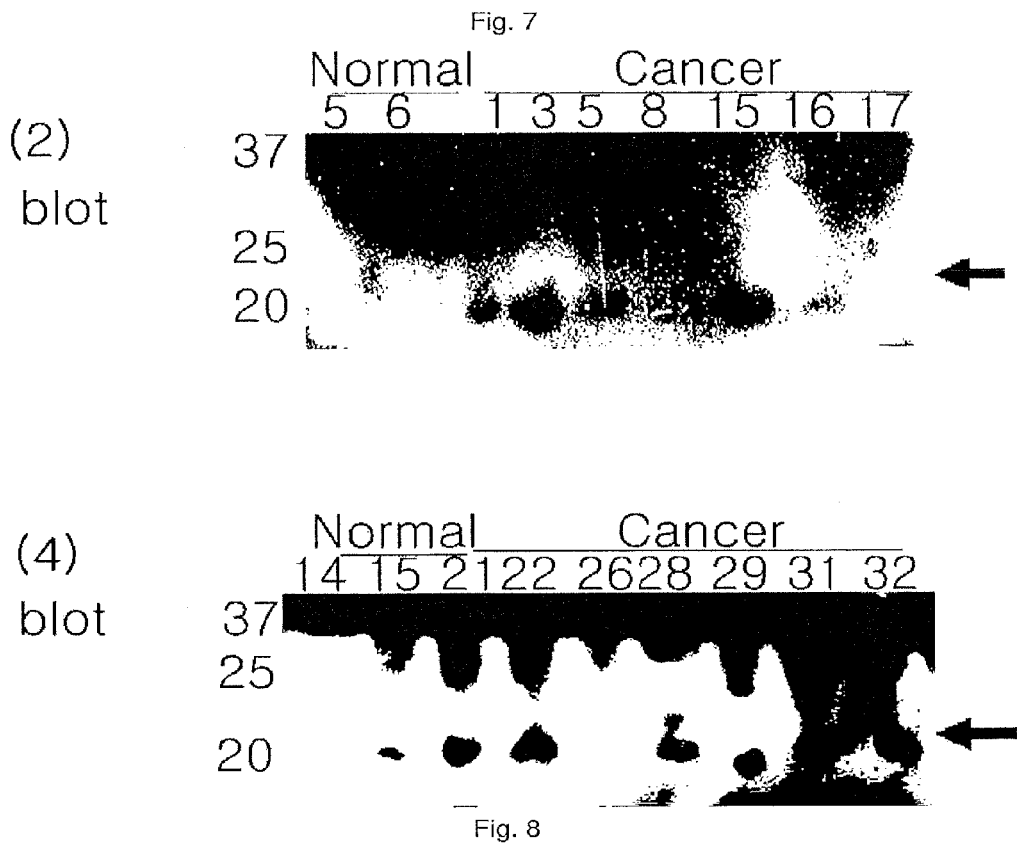

```
  1 MILFKQATYF ISLFATVSCG CLTQLYENAF FRGGDVASMY TPNAQYCQMR CTFHPRCLLF
 61 SFLPASSIND MEKRFGCFLK DSVTGTLPKV HRTGAVSGHS LKQCGHQISA CHRDIYKGVD
121 MRGVNFNVSK VSSVEECQKR CTNNIRCQFF SYATQTFHKA EYRNNCLLKY SPGGTPTAIK
181 VLSNVESGFS LKPCALSEIG CHMNIFQHLA FSDVDVARVL TPDAFVCRTI CTYHPNCLFF
241 TFYTNVWKIF SQRNVCLLKT SESGTPSSST PQENTISGYS LLTCKRTLPE PCHSKIYPGV
301 DFGGEELNVT FVKGVNVCQE TCTKMIRCQF FTYSLLPEDC KEEKCKCFLR LSMDGSPTRI
361 AYGTQGSSGY SLRLCNTGDN SVCTTKTSTR IVGGTNSSWG EWPWQVSLQV KLTAQRHLCG
421 GSLIGHQWVL TAAHCFDGLP LQDVWRIYSG ILNLSDITKD TPFSQIKEII IHQNYKVSEG
481 NHDIALIKLQ APLNYTFFQK PICLPSKGDT STIYTNCWVT GWGFSKEKGE IQNILQKVNI
541 PLVTNEECQK RYQDYKITQR MVCAGYKEGG KDACKGDSGG PLVCKHNGMW RLVGITSWGE
601 GCARREQPGV YTKVAFYMDW ILEKTQSSDG KAQMQSPA
```

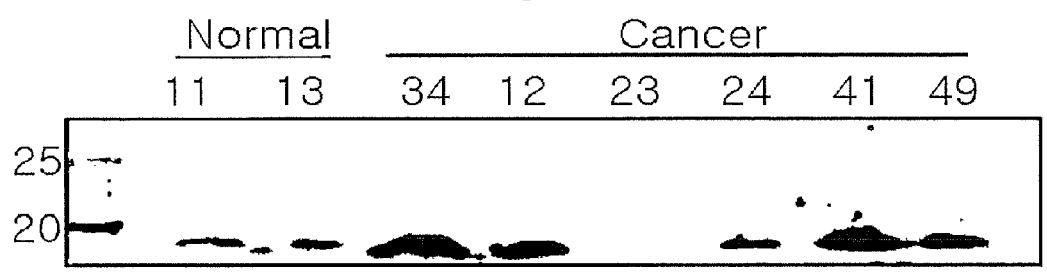
Fig. 9
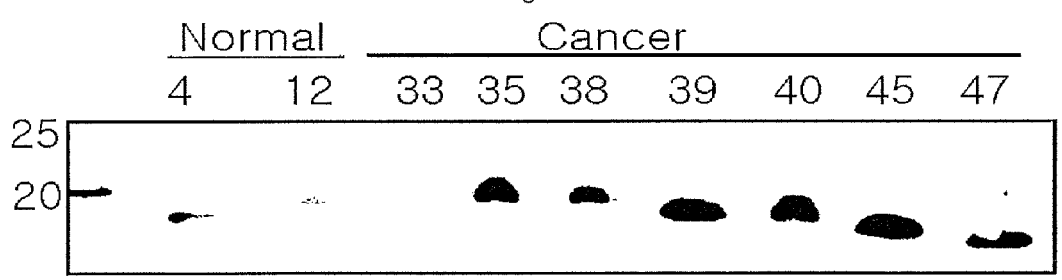
Fig. 10
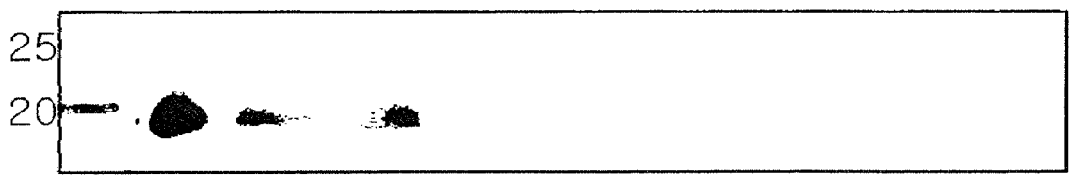

Fig. 11
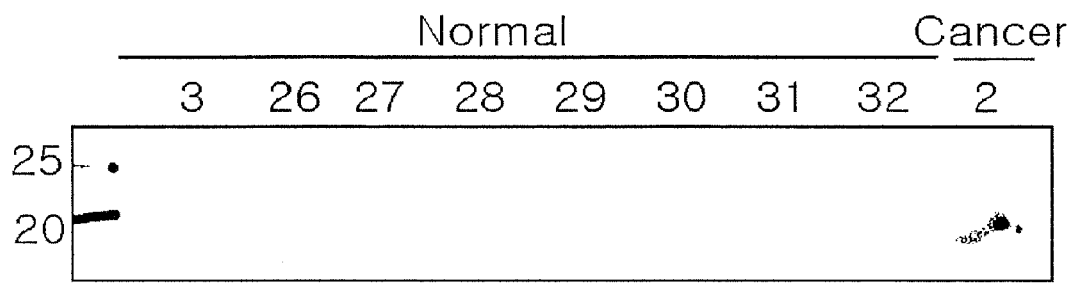
Fig. 12
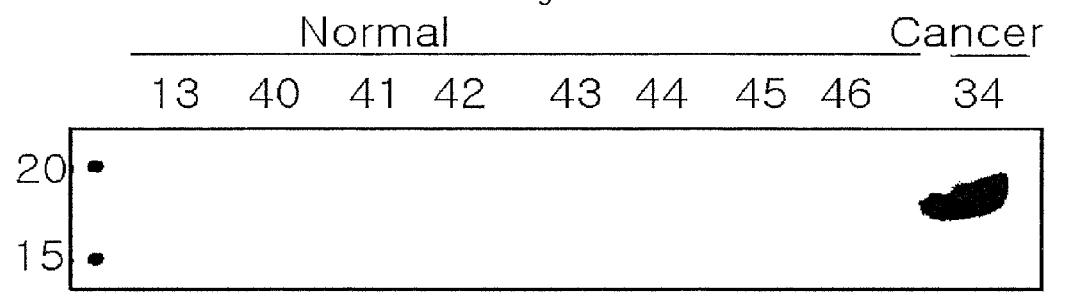
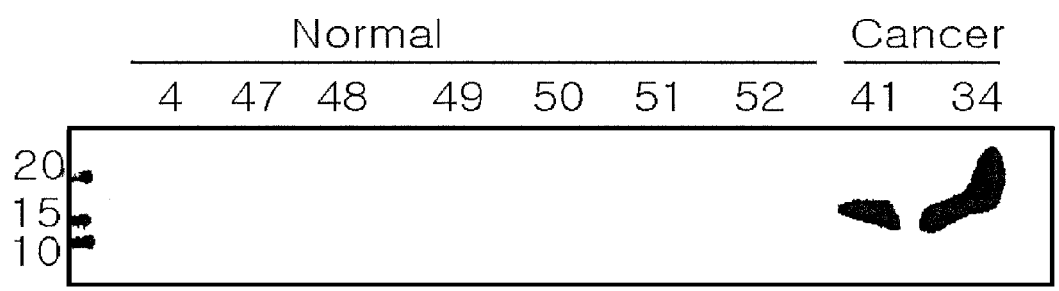

SEQUENCE LISTING

```
<160> NUMBER OF SEQ ID NOS: 1

<210> SEQ ID NO 1
<211> LENGTH: 638
<212> TYPE: PRT
<213> ORGANISM: Homo sapiens

<400> SEQUENCE: 1

Met Ile Leu Phe Lys Gln Ala Thr Tyr Phe Ile Ser Leu Phe Ala Thr
  1               5                  10                  15

Val Ser Cys Gly Cys Leu Thr Gln Leu Tyr Glu Asn Ala Phe Phe Arg
                 20                  25                  30

Gly Gly Asp Val Ala Ser Met Tyr Thr Pro Asn Ala Gln Tyr Cys Gln
             35                  40                  45

Met Arg Cys Thr Phe His Pro Arg Cys Leu Leu Phe Ser Phe Leu Pro
 50                  55                  60

Ala Ser Ser Ile Asn Asp Met Glu Lys Arg Phe Gly Cys Phe Leu Lys
 65                  70                  75                  80

Asp Ser Val Thr Gly Thr Leu Pro Lys Val His Arg Thr Gly Ala Val
                 85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
            115                 120                 125

Ser Lys Val Ser Ser Val Glu Glu Cys Gln Lys Arg Cys Thr Asn Asn
        130                 135                 140

Ile Arg Cys Gln Phe Phe Ser Tyr Ala Thr Gln Thr Phe His Lys Ala
145                 150                 155                 160
```

```
Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
    210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Ser Thr Pro Gln
            260                 265                 270

Glu Asn Thr Ile Ser Gly Tyr Ser Leu Leu Thr Cys Lys Arg Thr Leu
        275                 280                 285

Pro Glu Pro Cys His Ser Lys Ile Tyr Pro Gly Val Asp Phe Gly Gly
    290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Lys Cys Lys Cys Phe Leu Arg Leu Ser
            340                 345                 350

Met Asp Gly Ser Pro Thr Arg Ile Ala Tyr Gly Thr Gln Gly Ser Ser
        355                 360                 365

Gly Tyr Ser Leu Arg Leu Cys Asn Thr Gly Asp Asn Ser Val Cys Thr
    370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
                405                 410                 415

His Leu Cys Gly Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
    450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
        515                 520                 525

Gly Glu Ile Gln Asn Ile Leu Gln Lys Val Asn Ile Pro Leu Val Thr
    530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575
```

```
Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
        610                 615                 620

Thr Gln Ser Ser Asp Gly Lys Ala Gln Met Gln Ser Pro Ala
625                 630                 635
```

PLASMA KALLIKREIN FRAGMENTS AS DIAGNOSTIC BIOMARKERS FOR LUNG CANCERS

The present invention claims priority of Korean patent application no. 10-2007-0027541, international application number PCT/KR/2007/004322, U.S. patent application Ser. No. 13/494,215 (now abandoned) respectfully filed on Mar. 21, 2007, Sep. 6, 2007, and Jun. 12, 2012 in which all are incorporated herein by reference in their entirety.

TECHNICAL FIELD

The present invention relates to the use of a plasma kallikrein fragment as a diagnostic biomarker for lung cancer.

BACKGROUND ART

Lung cancer is the most common form of cancer in the world, which is estimated to account for 12.3% of all cancers and 17.8% of cancer-related deaths (Parkin, D. M., *Lancet Oncol* 2001, 2, 533-43). Also, the incidence of lung cancer and the resulting mortality rate in Korea are estimated to continue to increase. Despite the recent development of cancer therapy, the survival rate of lung cancer patients is very low. This is because the cancer is diagnosed at a late stage in most cases. Thus, there is an urgent need to develop markers which can diagnose lung cancer at an early state to increase the survival rate of lung cancer patients.

Meanwhile, human body fluids, such as blood and urine, are useful for recognizing the pathological conditions (conditions associated with tumors, immune responses and vascular diseases) of the body, because they can be easily collected for diagnosis and include secretory proteins which are expressed differently in abnormal and normal conditions. In addition, due to abundant serum proteins (such as albumin, IgG and transferrin), it is difficult to detect low abundant proteins which can be used as new biomarkers. A number of studies have attempted various approaches to reduce abundant serum proteins. Methods for removing the abundant serum proteins were introduced by some researchers and are generally classified into two categories. One of them is the use of an immunoaffinity HPLC column to reduce albumin, IgA, IgG, transferin, haptoglobin (HP) and antitrypsin (Okano, T. et al., *Proteomics* 2006, 6, 3938-48; Yu, K. H. et al., *J Proteome Res* 2005, 4, 1742-51). Another is the isolation of serum glycoproteins using hydrazide chemistry (Liu, T. et al., *J Proteome Res* 2005, 4, 2070-80) or lectin affinity (Yang, Z. et al., *J Chromatogr A* 2004, 1053, 79-88; Yang, Z. et al., *Proteomics* 2005, 5, 3353-66; Vosseller, K. et al., *Mol Cell Proteomics* 2006, 5, 923-34; Zhang, H. et al., *Mol Cell Proteomics* 2005, 4, 144-55).

Two recent studies reported proteins expressed differently between healthy person's serum and lung cancer patient's serum using 2-DE and MALDI-TOF (Maciel, C. et al., *J Exp Ther Oncol* 2005, 5, 31-8) or 2-DE and LC-MS/MS (Okano, T. et al., *Proteomics* 2006, 6, 3938-48), and NSE, CEA and CYFRA 21-1 are currently known as serum markers for lung cancer. However, the sensitivity and specificity thereof as lung cancer markers are not sufficient (Tarro, G. et al., *J Cell Physiol* 2005, 203, 1-5). For this reason, the development of novel biomarkers specific for lung cancer is urgently needed.

DISCLOSURE OF INVENTION

Technical Problem

Accordingly, the present inventors have studied to develop novel diagnostic markers capable of diagnosing lung cancer and, as a result, have identified proteins, which are specifically expressed only in the sera of lung cancer patients, and thus can be used as biomarkers for diagnosing lung cancer, by separating glycoproteins from the sera of lung cancer patients using a multi-lectin affinity column, removing the glycans of the glycoproteins by enzymatic treatment, collecting peptides from the proteins by in-gel trypsin digestion, and then analyzing the peptides by LC-MS/MS, thereby completing the present invention.

It is therefore an object of the present invention to provide diagnostic markers for lung cancer, separated from serum glycoproteins.

Technical Solution

To achieve the above object, in one aspect, the present invention provides diagnostic markers for lung cancer, separated from serum glycoproteins.

In another aspect, the present invention provides a composition for diagnosing lung cancer, which comprises an antibody binding specifically to the diagnostic marker.

In still another aspect, the present invention provides a composition for diagnosing lung cancer, which comprises a primer or probe specific for a nucleic acid encoding the diagnostic marker.

In still another aspect, the present invention provides a method of diagnosing lung cancer using the diagnostic marker.

In yet another aspect, the present invention provides a method for identifying the diagnostic markers.

Hereinafter, the present invention will be described in detail.

As used herein, the term "diagnosis" refers to the determination of the presence or properties of pathological conditions. For the purpose of the present invention, the term "diagnosis" means determining the incidence of lung cancer.

As used herein, the term "lung cancer" means a malignant tumor occurring in the lungs.

As used herein, the term "diagnostic marker" is intended to indicate a substance capable of diagnosing lung cancer by distinguishing lung cancer cells from normal cells, and includes organic biomolecules, which increase in lung cancer cells compared to normal cells or in cancer subjects compared to normal subjects. Examples of the organic biomolecules include, but are not limited to, polypeptides, proteins, nucleic acids, lipids, glycolipids, glycoproteins and sugars. In the present invention, the organic biomolecules preferably refers to glycoproteins.

In order to discover novel diagnostic markers for lung cancer, the present inventors have identified glycoproteins which are expressed differently between the sera of lung cancer patients and the sera of normal persons. For this purpose, a multi-lectin affinity column was used to glycoprotein from serum, the glycoprotein was deglycosylated by enzymatic treatment, and then treated with trypsin, thus obtaining a peptide. The obtained peptide was separated by liquid chromatography, while it was analyzed with an ion trap mass spectrometer (LC-MS/MS). The LC-MS/MS data were searched against the IPI human protein database using computer program, thus confirming glycoproteins present in the sera of lung cancer patients. The glycoprotein was compared with a glycoprotein derived from the sera of normal persons to confirm that it is present specifically in the sera of lung cancer patients, and thus can be used as a diagnostic marker for lung cancer. An experimental method for identifying a diagnostic marker in the sera of lung cancer patients according to a preferred embodiment of the present invention is shown in FIG. 1.

In one Example of the present invention, a total of six blood samples were collected from lung cancer patients (three samples) and normal persons (three samples) and centrifuged to obtain serum samples (see Example <1-1>). Glycoproteins were isolated from the obtained serum samples using a multi-lectin affinity column and concentrated by acetone precipitation (see Example <1-2>).

In one Example of the present invention, the eluate (concentrated glycoprotein) and flow-through fractions, obtained by the multi-lectin affinity column, were subjected to Coomassie brilliant straining and GelCode glycoprotein staining to determine the efficiency of the multi-lectin affinity column for glycoprotein separation (see Example <1-3>) and, as a result, it could be seen that, by the multi-lectin affinity column, serum glycoproteins were concentrated and albumin was removed (see FIG. 2).

Accordingly, in the present invention, the above-obtained concentrated serum glycoproteins were treated with peptide-N-glycosidase F (PNGase F) to remove the sugar moieties and subjected to 1D-SDS PAGE (see Example <2-1>), and the resulting materials were subjected to in-gel digestion, thus obtaining peptide mixtures (see Example <2-2>). The obtained peptide mixtures were analyzed with LC-MS/MS, thus identifying 38 proteins, the expression of which was increased in the sera of lung cancer patients compared to the sera of normal persons (see Example 3).

Some of the 38 identified proteins were reported that they can be used as lung cancer markers in the serum or plasma of lung cancer patients. Examples thereof include heptoglobin (HP), inter-alpha-trypsin inhibitor H4 (ITI-H4), complement C3 precursor, leucin-rich alpha 2 glycoprotein and the like. The proteins other than them are not yet known as lung cancer markers or biomarkers.

Accordingly, the present invention provides a diagnostic marker for lung cancer, which comprises a protein selected from the group consisting of complement component c8 beta chain precursor, protein s100-a9, C4b-binding protein alpha chain precursor, isoform 2 of apolipoprotein-11 precursor, protein s100-a8, proteins similar to cavia porcellus phosphatidic acid phosphatase 2A mRNA, complement component c9 precursor, inter-alpha-trypsin inhibitor heavy chain h3 precursor, Flj00385 protein (fragment), coagulation factor xii precursor, Ig alpha-2 chain c region), complement component c8 alpha chain precursor, corticosteroid-binding globulin precursor, clusterin precursor, gamma-g globin, serum amyloid p-component precursor, plasma kallikrein fragment (KLKB1 fragment), Ighal protein, heparin cofactor 2 precursor, 16 kDa protein, Ig kappa chain v-iii region gol, complement factor I precursor, hemoglobin subunit beta, proteins similar to tripartite motif protein 49, isoform 1 of complement factor b precursor (fragment), alpha-1-antitrypsin precursor, carboxypeptidase n subunit 2 precursor, complement factor h-related protein 3 precursor, plasma protease c1 inhibitor precursor, Ig kappa chain c region, alpha 2 macroglobulin variant, dermcidin precursor, complement c5 precursor and pregnancy zone protein precursor, which are shown in Table 4 below.

Preferably, the present invention provides a diagnostic marker, which contains inter-alpha-trypsin inhibitor heavy chain h3 precursor or plasma kallikrein fragment (KLKB1 fragment).

The diagnostic marker is specifically expressed only in the sera of lung cancer patients.

In one Example of the present invention, whether inter-alpha-trypsin inhibitor heavy chain h3 precursor (ITI-H3) is specifically expressed only in the sera of lung cancer patients was analyzed by Western blotting (see Example 4). As a result, it could be seen that the protein was expressed highly in the sera of lung cancer patients compared to in the sera of normal persons (see FIG. 4).

In another Example of the present invention, whether plasma kallikrein fragment (KLKB1 fragment) is specifically expressed only in the sera of lung cancer patients was analyzed by Western blotting (see Example 6). As a result, it could be seen that a band having a size of 15-20 kDa was detected only in the sample of lung cancer patients at a high level (see FIG. 5). This was thought to be because the heavy chains of KLKB1 were partially cleaved.

In other Examples of the present invention, a Western blot was performed on 8 normal persons and 28 patients using an antibody specific for the plasma kallikrein fragment (see Examples 7 and 8). It could be seen that a 18-kDa fragment was weakly detected in one person of the 8 normal persons and was detected in 25 patients of the 28 patients at high levels (see FIGS. 6 and 7). Also, a Western blot was additionally performed on 24 lung cancer patients (see FIG. 9). As a result, in the normal persons, the KLKB1 fragment was not almost detected or was detected at low levels, but in the lung cancer patients, the KLKB1 fragment was detected in 20 patients of the 24 patients at high levels (see FIGS. 9 to 12).

From the results of Example 7 to Example 9, it could be seen that the 18 kDa fragment was detected in 45 patients of the 52 lung cancer patients, and thus had a sensitivity of 87% and a specificity of 67%. On the other hand, the levels of the 18 kDa fragment in the normal persons were always lower than that in the lung cancer patients.

Meanwhile, it is known that the plasma kallikrein fragment consists of a total of 619 amino acids except for 19 signal peptides among 638 amino acids (see SEQ ID NO: 1) and is originally synthesized in the liver. It is a protein known to be involved in blood coagulation, fibrinolysis and kinin formation. It consists of 4 heavy chains (amino acid residues 20 to 390) and 1 light chain (amino acid residues 391-638) (see FIG. 8), in which the heavy chains are classified into H1, H3 and H4 domains.

The antibody specific for the plasma kallikrein fragment, used in the Western blot in Example of the present invention, was prepared using an epitope of amino acid residues of 361-400 of plasma kallikrein, which corresponded to the latter part of the H4 domain. Thus, the fragment detected in Example of the present invention is believed to be a fragment containing the H4 domain of KLKB1.

The detection of the inventive diagnostic marker in biological samples can be performed either using an antibody binding specifically to the diagnostic marker or using a primer or probe specific for a nucleic acid encoding the diagnostic marker.

Accordingly, the present invention provides a composition for diagnosing lung cancer, which contains an antibody bonding specifically to the diagnostic marker of the present invention.

Preferably, the present invention provides a composition for diagnosing lung cancer, which contains an antibody specific for inter-alpha-trypsin inhibitor heavy chain h3 precursor (ITI-H3) or plasma kallikrein fragment.

As used herein, the term "antibody" refers to a protein molecule which is directed specifically to an antigenic site. Examples of antibodies for use in the present invention include monoclonal or polyclonal antibodies, immunologically active fragment (e.g., Fab or (Fab)$_2$ fragments), antibody heavy chains, humanized antibodies, antibody light chains, genetically engineered single chain Fv molecules, and chimeric antibodies.

Because the proteins known in Table 4 are known proteins, the antibodies that are used in the present invention can be prepared using the known proteins as antigens according to any conventional method widely known in the immunological field. The protein that is used as an antigen for the antibody according to the present invention can be extracted naturally or synthesized. Alternatively, it can be prepared by a recombinant method based on DNA sequences. When the gene recombinant technology is used, the antigen protein can be prepared by inserting into a suitable expression vector a nucleic acid encoding the protein, culturing host cells transformed with the recombinant expression vector so as to express the target protein, and then collecting the target protein from the cultured cells.

For example, polyclonal antibodies can be produced by injecting an antigen into an animal and collecting blood from the animal to obtain an antibody-containing serum. Such antibodies can be prepared using various warm-blooded animals, such as horses, cattle, goats, sheep, dogs, fowls, turkeys, rabbits, mice or rats.

Monoclonal antibodies may be prepared in accordance with a fusion method (Kohler and Milstein, *European Journal of Immunol.*, 6:511-519 (1976)), a recombinant DNA method (U.S. Pat. No. 4,816,56) or a phage antibody library (Clackson et al, Nature, 352:624-628 (1991); and Marks et al, *J. Mol. Biol.*, 222:58, 1-597 (1991)).

The diagnostic composition of the present invention may comprise, in addition to the antibody specific for the protein, reagents which are used for immunological assays. The immunological assays may include methods capable of measuring the binding of an antigen to the antibody of the present invention. These methods are known in the art and include, for example, immunocytochemical assays, immunohistochemical assays, radioimmunoassays, ELISA (enzyme linked immunoabsorbent assay), immunoblotting, Farr assays, precipitin reaction, turbidimetry, immunodiffusion, counter-current electrophoresis, single radical immunodiffusion and immunofluorescence.

Reagents which are used in the immunological assays include a labeling substance capable of emitting detectable signals, a solubilizer and a washing agent. Furthermore, if the labeling substance is enzyme, a substrate capable of measuring enzymatic activity and a reaction stopping agent may be used. The labeling substance capable of emitting detectable signals enabling quantitative or qualitative measurement of the formation of antigen-antibody complexes include enzymes, and examples thereof include enzymes, fluorescent substances, ligands, luminescent substances, microparticles, redox molecules and radioactive isotopes. The enzymes may include β-glucuronidase, β-D-glucosidase, β-D-galactosidase, urease, peroxidase, alkaline phosphatase, acetylcholine esterase, glucose oxidase, hexokinase, malate dehydrogenase, glucose-6-phosphate dehydrogenase, invertase and the like. The fluorescent substances include fluorescein, isothiocyanate, rhodamine, phycoerythrin, phycocyanin, allophycocyanin, fluorescein, isothiocyanate, and the like. The ligands include biotin derivatives, and the luminescent substances include acridinium ester, luciferin, and luciferase acrydinium ester. The microparticles include colloidal gold, and colored latex, and the redox molecules include ruthenium complexes, viologen, quinone, Ti ions, Cs ions, diimide, 1,4-benzoquinone, hydroquinone, and the like. The radioactive isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$ and the like. However, in addition to the above-exemplified substances, any substance can be used, as long as it can be immunological assays.

Also, to detect the presence of the marker protein of the present invention, a peptide binding specifically to the marker protein of the present invention may be used. Accordingly, the present invention provides a composition for diagnosing lung cancer, which contains a peptide binding specifically to one selected from among the proteins shown in Table 4. Preferably, the peptide may consist of 7-35 amino acids derived from the marker protein of the present invention.

Also, the diagnostic composition of the present invention can be immobilized on a suitable carrier or support in order to enhance the rapidness and convenience of diagnosis (*Antibodies*: A Laboratory Manual, Harlow & Lane; Cold Spring-Harbor, 1988). Examples of suitable carriers or supports include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, cups and flat packs. In addition, other solid substrates include cell culture plates, ELISA plates, tubes and polymeric membranes. The support material may have any possible configuration including spherical (e.g., bead), cylindrical (e.g., inside surface of a test tube or well, or flat (e.g., sheet, test strip).

Preferably, the inventive composition for diagnosing lung cancer can be provided in the form of a diagnostic kit or a protein chip.

The diagnostic kit can be provided in the form of a lateral flow assay kit based on immunochromatography to detect a specific protein in a sample. The lateral flow assay kit comprises: a sample pad to which a sample is applied; a releasing pad which is coated with an antibody for detection; a developing membrane (e.g., nitrocellulose) or strip in which the sample is transferred and separated and an antigen-antibody reaction occurs; and an absorption pad. Also, the diagnostic kit of the present invention may also be in the form of, but is not limited to, a rapid kit or an ELISA kit.

In the protein chip, either an antibody specific for the inventive marker protein or a peptide binding specifically to the inventive marker protein is generally attached to a slide glass surface treated with a specific reagent, such that the protein binding specifically to the antigen or the peptide can be detected by antigen-antibody reactions or protein-protein interactions. It is used to detect various different kinds of antibodies or peptides and may comprise kallikrein fragment peptides or antibodies.

In another aspect, the present invention provides a composition for diagnosing lung cancer, which contains a primer or probe specific for a nucleic acid encoding the diagnostic marker protein of the present invention.

Preferably, the present invention provides a composition for diagnosing lung cancer, which contains a primer or probe specific for a nucleic acid encoding either inter-alpha-trypsin inhibitor heavy chain h3 precursor (ITI-H3) or plasma kallikrein fragment (KLKB1 fragment).

The detection of a specific nucleic acid using a primer can be performed by amplifying the sequence of a target gene using an amplification method such as PCR, and then analyzing the amplification of the gene using a method known in the art. Also, the detection of a specific nucleic acid using a probe can be performed by bringing a sample nucleic acid into contact with the probe in suitable conditions, and then analyzing the presence of a hybridized nucleic acid.

The term "primer", as used herein, refers to a short nucleic acid sequence having a free hydroxyl group, which is able to undergo base-pairing interaction with a complementary template and serves as a starting point for replicating the template strand. For example, the primer of the present invention can be chemically synthesized using a method known in the art, such as the phosphoramidite solid support method.

As used herein, the term "probe" refers to a nucleic acid fragment of RNA or DNA consisting of a few or a few hundreds bases, which can bind specifically to mRNA. It is labeled such that the presence of a specific mRNA can be detected. The probe can be prepared in the form of oligonucleotide probes, single-stranded DNA probes, double-stranded DNA probes and RNA probes and may be labeled with biotin, FITC, rhodamine, DIG or radioactive isotopes.

Also, the probe may be labeled with a detectable label, for example, a radioactive label which provides a suitable signal and has a sufficient half life. The labeled probe can be hybridized to a nucleic acid on a solid support as described in the literature (Sambook et al., *Molecular Cloning*, A Laboratory Mannual, 1989).

Examples of the methods of detecting a specific nucleic acid using said probe or primer include, but are not limited to, polymerase chain reaction (PCR), DNA sequencing, RT-PCR, primer extension method (Nikiforeov et al., *Nucl Acids Res* 22, 4167-4175, 1994), oligonucleotide ligation analysis (Nickerson et al., *Pro Nat Acad Sci USA*, 87, 8923-8927, 1990), allele-specific PCR (Rust et al., *Nucl Acids Res*, 6, 3623-3629, 1993), RNase mismatch cleavage (Myers et al., *Science*, 230, 1242-1246, 1985), single strand conformation polymorphism (Orita et al., *Pro Nat Acad Sci USA*, 86, 2766-2770, 1989), simultaneous analysis of SSCP and heteroduplex (Lee et al., *Mol Cells*, 5:668-672, 1995), denaturation gradient gel electrophoresis (DGGE, Cariello et al., *Am J Hum Genet*, 42, 726-734, 1988), denaturing high performance liquid chromatography (Underhill et al., *Genome Res*, 7, 996-1005, 1997), hybridization reactions and DNA chips. Examples of the hybridization reactions include Northern hybridization (Maniatis T. et al., *Molecular Cloning*, Cold Spring Habor Laboratory, NY, 1982), in situ hybridization (Jacquemier et al., *Bull Cancer*, 90:31-8, 2003) and microarrays (Macgregor, *Expert Rev Mol Diagn* 3:185-200, 2003).

The inventive composition for diagnosing lung cancer may additionally comprise reagents which are generally used in the methods for detecting nucleic acids. For example, the composition may comprise deoxynucleotide triphosphate (dNTP), heat-resistant polymerase and metal ion salts such as magnesium sulfate, which are required in PCR reactions, as well as dNTP and sequenase, which are required in sequencing.

Preferably, the inventive composition for diagnosing lung cancer may be provided in the form of a diagnostic kit or microarray.

Examples of the diagnostic kit or microarray include, but are not limited to, RT-PCR kits containing each of primers specific for the inventive marker gene, and DNA chips comprising a substrate having attached thereto the cDNA or oligonucleotide of the inventive marker gene.

In another aspect, the present invention provides a method of diagnosing lung cancer using the diagnostic marker of the present invention.

Preferably, the diagnostic method of the present invention comprises the steps of: (a) bringing a biological samples into contact with an antibody binding specifically to the diagnostic marker of the present invention; and detecting the formation of an antigen-antibody complex.

The term "biological sample" or "sample" in the step (a) refers to blood or other liquid samples of biological origin. Preferably, the biological sample or sample may be whole blood, plasma or serum. The sample is collected from animals, preferably mammals, and most preferably humans. The sample can be pretreated before use in detection. For example, the pretreatment can involve filtration, distillation, extraction, concentration, inactivation of interfering components, the addition of reagents, and the like. In addition, nucleic acids and proteins may be isolated from the samples and used in detection.

The term "antigen-antibody complex in the step (b) refers to a combination of a specific protein in a biological sample with an antibody binding specifically to the specific protein.

The detection of the formation of the antigen-antibody complex in the step (b) can be performed using a method known in the art. Examples of the detection method include, but are not limited to, rapid diagnostic kits, RIA (radioimmunoassay), RIPA (radioimmunoprecipitation assay), IFA (immunoflourescence assay), EILSA (enzyme-linked immunosorbent assay) and Western blot.

Preferably, the inventive method for diagnosing lung cancer may comprise the steps of: (a) removing a plasma kallikrein fragment and the heavy chain precursor form thereof from the serum of a subject; (b) bringing the serum, from which the plasma kallikrein fragment and the heavy chain precursor form thereof had been removed in the step (a), into contact with an antibody specific for a region comprising the H4 domain of the plasma kallikrein fragment; and (c) detecting the formation of an antigen-antibody complex.

The removal of the plasma kallikrein fragment and the heavy chain precursor form thereof in the step (a) can be performed by bringing the serum into contact with an antibody specific for the total plasma kallikrein fragment or by using molecular size separation columns.

The antibody specific for the total plasma kallikrein fragment may be a polyclonal or monoclonal antibody prepared using, as an antigen, the total plasma kallikrein fragment having an amino acid sequence represented by SEQ ID NO: 1.

The antibody specific for the region comprising the H4 domain of the plasma kallikrein fragment in the step (b) may be prepared using an epitope of amino acid residues 361-400 of the amino acid represented by SEQ ID NO: 1.

Meanwhile, the detection of the formation of the antigen-antibody complex in the step (c) can be performed according to the above-described method, and if a fragment having a size of about 15-20 kDa, and preferably about 18 kDa, is detected in a sample, the sample would be diagnosed as lung cancer.

In another aspect, the present invention provides a method for identifying a diagnostic marker for lung cancer, the method comprising the steps of: (a) isolating glycoproteins from a serum sample using a multi-lectin affinity column; (b) concentrating the isolated glycoproteins of step (a) by acetone precipitation; (c) deglycosylating the concentrated glycoproteins of step (b) by enzymatic treatment; (d) subjecting the decosylated proteins of step (c) to SDS-PAGE; (e) collecting peptides from the proteins by in-gel trypsin digestion; and (f) analyzing the peptides of step (e) by LC-MS/MS to identify proteins which are specifically expressed only in the sera of lung cancer patients compared to the sera of normal persons.

Advantageous Effects

The diagnostic markers for lung cancer according to the present invention are highly expressed specifically in the sera of lung cancer patients at high levels, and thus are very useful for diagnosing lung cancer and estimating disease progression and treatment.

BRIEF DESCRIPTION OF THE DRAWINGS

FIG. 1 is a schematic diagram showing an ultra high speed method for analyzing a human serum protein according to the method of the present invention.

FIG. 2 shows Coomassie brilliant straining results (A) and GelCode staining results (B) for a glycoprotein isolated from human serum using a multi-lectin affinity column, and Coomassie brilliant straining results (C) for a deglycosylated serum glycoprotein. In FIGS. 2A and 2B, lane 1: size marker; lanes 2, 4 and 6: normal flow-through samples; lanes 3, 5 and 7: normal eluate samples; lanes 8, 10 and 12: cancer flow-through samples; lanes 9, 11 and 13: cancer eluate samples; and in FIG. 2C, lane 1: size marker; lanes 2 to 4: normal samples; and lanes 5 to 7: cancer samples.

FIG. 5 shows the results of Western blotting of a plasma kallikrein fragment in the sera of lung cancer patients and normal persons or in glycoproteins concentrated from the sera.

FIG. 6 shows the results of Western blotting of a plasma kallikrein fragment in the whole sera of normal persons or lung cancer patients 50-60 years old.

FIG. 7 shows the results of Western blotting of a plasma kallikrein fragment in the whole sera of normal persons or lung cancer patients more than 65 years old.

FIG. 8 shows the amino acid sequence of a plasma kallikrein fragment (SEQ ID NO: 1). In FIG. 8, green: signal peptide; blue: heavy chain; and bold: H4 domain.

FIG. 9 shows the results of Western blotting of a plasma kallikrein fragment in the whole sera of normal persons and lung cancer patients.

FIG. 10 shows the results of Western blotting of a plasma kallikrein fragment in the whole sera of normal persons and lung cancer patients.

FIG. 11 shows the results of Western blotting of a plasma kallikrein fragment in the whole sera of normal persons and lung cancer patients.

FIG. 12 shows the results of Western blotting of a plasma kallikrein fragment in the whole sera of normal persons and lung cancer patients.

BEST MODE FOR CARRYING OUT THE INVENTION

Figure 3:
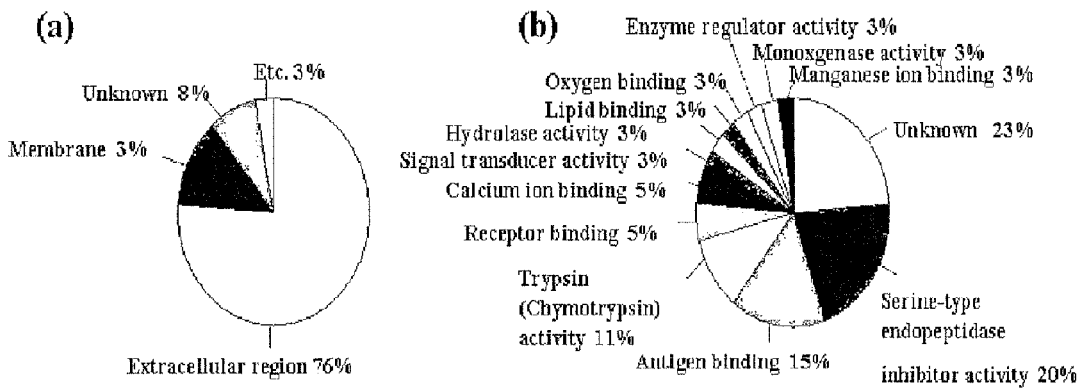
FIG. 3 shows classification according to the intracellular location (A), molecular function (B) and physiological process of the inventive diagnostic marker for lung cancer.

Hereinafter, the present invention will be described in further detail. It is to be understood, however, that these examples are illustrative only, and the scope of the present invention is not limited thereto.

Example 1

Isolation and Deglycosylation of Glycoprotein from Human Serum

<1-1> Serum Sample 6 blood samples were collected from 3 lung adenocarcinoma patients and 3 healthy normal persons among 65-year-old smoking men under consent in Kyungpook National University Hospital, Korea (Table 1). The blood samples were centrifuged at 4° C. at 12000 rpm for 10 minutes to collect sera, which were then stored at −70° C. before use in experiments.

TABLE 1

Features of lung cancer patients and normal patients

|  | Lung cancer group | Normal group |
| --- | --- | --- |
| Number of subjects | 3 | 3 |
| Clinical history | Lung cancer | Healthy |
| Sex | Men | Men |
| Age | 64 | 64 |
| Smoking | Smokers | Smokers |

<1-2> Isolation and Concentration of Glycoproteins Using Multi-Lectin Affinity Column A multi-lectin affinity column was used to isolate and concentrate glycoproteins from the serum samples obtained in Example <1-1>. The multi-lectin affinity column (Qiagen, USA) was packed with ConA (concanavalinA), LCH (lentil lectin), GNA (snowdrop lectin), WGA (wheat germ agglutinin), SNA (elderberry lectin), MAL (*maackia amurensis* lectin), AIL (jacalin) and PNA (peanut agglutinin). ConA, LCH and GNA could capture N-glycosylated proteins, and WGA, SNA and MAL could bind to sialic acid modified proteins. Also, AIL and PNA could isolate 0-glycosylated proteins. After centrifugation at 500 rpm for 2 minutes, the spin column was supplemented with 500 μl of binding buffer, 50 μl of each serum obtained in Example <1-1> was added and diluted in 500 μl of protease inhibitor solution-containing binding buffer, and the dilution was loaded into the spin column and incubated at room temperature for 1 minute.

To measure the efficiency of the column, the column was centrifuged at 500 rpm for 2 minutes, and the flow-through fraction was collected. An elution buffer was added to the column to collect the eluate, which was then concentrated and desalted by acetone precipitation.

<1-3> Coomassie Brilliant Staining and GelCode Glycoprotein Staining

In order to measure the efficiency of the multi-lectin affinity column for glycoprotein separation, the eluate (concentrated glycoprotein) and flow-through fractions, obtained by the multi-lectin affinity column in Example <1-2>, were subjected to Coomassie brilliant straining and GelCode sugar protein staining.

The Coomassie brilliant straining was performed in the following manner. Each of the eluate and flow-through fractions, obtained in Example <1-2>, was electrophoresed on gel, and then the gel was washed three times with ddH$_2$O for 5 minutes and stained with Bio-safe Coomassie G250 stain (Bio-Rad) at room temperature for 1 hour with gentle stirring. After incubation, the gel was desalted with ddH$_2$O and supplemented three times with ddH$_2$O one time every 10 minutes.

The GelCod glycoprotein staining (PIERCE) was performed according to the manufacturer's instruction. Specifically, the gel was immersed and fixed in 50% methanol for 30 minutes, and then washed twice with 100 ml of 3% acetic acid for 10 minutes. The washed gel was incubated in oxidizing solution for 15 minutes and washed with 3% acetic acid for 5 minutes, and the incubation and washing processes were repeated three times. A GelCod glycoprotein staining reagent was added to the gel and stirred slowly for 15 minutes.

Finally, the stained gel was washed sequentially with 3% acetic acid and distilled water.

In the experimental results, some of nonstained proteins in the flow-through fractions derived from the lung cancer patients and the normal persons, particularly proteins having sizes of more than about 40 kDa and 100 kDa, were detected in the eluate of the multi-lectin affinity column. A serum albumin band was observed in all the flow-through fractions, but was weakly stained by the Coomassie staining. Such experimental results revealed that low abundant proteins were concentrated in the eluate of the multi-lectin affinity column (FIG. 2A). Also, it was shown that the proteins in the eluate were more clearly stained by the GelCod glycoprotein staining compared to those in the flow-through fractions (FIG. 2B). Accordingly, it could be seen that the multi-lectin affinity column was an efficient tool for the concentration of serum glycoprotein and the removal of albumin.

Mode for the Invention

Example 2

Deglycosylation of Glycoproteins and Preparation of Peptides

<2-1> Deglycosylation of Glycoproteins

The serum glycoproteins concentrated in Example 1 were treated with peptide-N-glycosidase F (PNGase F) to remove the sugar moieties and were subjected to 1D-SDS PAGE.

15 μg of the concentrated glycoproteins were denatured in a buffer, containing 100 mM mercaptoethanol and 2% octyl beta-D-glucopyranoside, at 100° C. for 10 minutes, and were cooled at room temperature. Then, the proteins were incubated in a reaction buffer, containing 5 μl of PNGase F (Sigma, Germany), at 37° C. for 3 hours. The deglycosylated proteins were loaded onto SDS-PAGE to separate the samples and were subjected to Coomassie brilliant straining. The SDS-PAGE results are shown in FIG. 2C.

<2-2> In-Gel Digestion

The gel Coomassie-stained in Example <2-1> was cleaved, and the resulting protein bands were desalted by treatment with 75 mM ammonium bicarbonate/40% ethanol (1:1). After desalting, a sufficient amount of DTT solution (5 mM dithiothreitol/25 mM ammonium bicarbonate) was added to the tube and incubated at 60 C for 3 minutes. After removal of the liquid from the gel, the gel pieces were cooled at room temperature. For alkylation of the proteins, the gel was incubated in 55 mM iodoaceto amide at room temperature for 30 minutes, and then the gel pieces were dewatered with 100% acetonitrile and dried. The gel pieces were expanded in 10 μl of 25 mM ammonium bicarbonate buffer, containing 20 μg/ml of modified sequencing grade trypsin (Roche Applied Science), and were incubated at 37° C. overnight for trypsin degradation. The peptide mixture produced by trypsin was eluted with 0.1% formic acid for LC-MS/MS analysis.

Example 3

LC-ESI-MS/MS Analysis

<3-1> LC-ESI-MS/MS

The peptide mixture produced in Example 2 was analyzed in the following manner using LC-MS/MS. The LC-MS/MS was performed using a Thermo Finnigan's ProteomeX workstation LTQ linear ion trap MS (Thermo Electron, San Jose, Calif., USA) equipped with nanospray ionization sources (NSI sources, San Jose, Calif.). 12 μl of the peptide mixture was injected and loaded into a peptide trap cartridge (Agilent, Palo Alto, Calif.). The trapped peptide was eluted using a 10-cm reversed-phase PicoFrit column (5 μm, 300 Å diameter C18) packed in a housing and was separated by gradient elution in a reverse phase column (RP column). As the mobile phase, each of solutions A ($H_2O$) and B (acetonitrile, ACN) was used, and the solutions all contained 0.1% (v/v) formic acid. The flow rate was maintained at 200 nL/min.

The gradient elution started with 2% mobile phase, and linear gradient elution was performed such that the mobile phase reached 60% within 50 minutes. Then, the mobile phase B reached 80% within 5 minutes, and then the mobile phase A reached 100% within 15 minutes.

The data-dependent acquisition mode was enabled (m/z 300-1800), and each full MS scan was followed by five MS/MS scans with the 30 s dynamic exclusion option on. The spray voltage and ion transfer tube temperature were set at 1.8 kV and 160 C, respectively. The normalized collision energy was set at 35%. The LC-MS/MS analysis was performed independently twice of each sample.

<3-2> Data Analysis

The MS/MS data base obtained in Example <3-1> were searched against the IPI human protein database using the SEQUEST algorithm (Thermo Electron, San Jose, Calif.) contained in the BioWorks software (version 3.2). The database searching permitted modification of cysteine (carboxyamidomethylation, 57 Da), variable modification of methionine (oxidation, 16 Da), peptide mass tolerance of 1.5 Da, and fragment mass tolerance of 1 Da.

The SEQUEST results were filtered by Xcorr versus charge state X. Xcorr values of 1.9 for singly charged ions, 2.2 for doubly charged ions, and 3.75 for triply charged ions were considered a match. The present inventors set Delta Cn=0.1, Rsp=4 and the probability limit 0.001. Proteins were identified based on the identity of the corresponding peptide(s). Additional filtering was carried out for proteins that scored more than ten, and proteins for which there were more than two corresponding peptides.

The present inventors used NetNGlyc 1.0 and NetOGlyc 3.1 for statistical analysis of N- and O-linked glycosylation sites, respectively, and an in-house informatics tool, ProtAn, was used for subtractive proteome analysis.

In the experimental results, 74, 121 and 80 proteins were identified in two repeated experiments for three normal samples, respectively, and 99, 115 and 101 proteins were identified in two repeated experiments for three cancer samples. The proteins identified by the LC-MS/MS analysis were 65.6-76.1% in the cancer samples and the normal samples (see Table 2).

TABLE 2

Number of proteins identified by LC-MS/MS analysis

| Samples | First protein ID | Second protein ID | Common protein | Reproducibility (%) |
| --- | --- | --- | --- | --- |
| Normal sample 1 (N1) | 95 | 86 | 74 | 69.2 |
| Normal sample 2 (N2) | 133 | 147 | 121 | 76.1 |
| Normal sample 3 (N3) | 95 | 107 | 80 | 65.6 |
| Cancer sample 1 (C1) | 121 | 120 | 99 | 69.7 |
| Cancer sample 2 (C2) | 127 | 141 | 115 | 75.2 |
| Cancer sample 3 (C3) | 112 | 128 | 101 | 72.7 |

Also, to examine the efficiency of concentration of glycoproteins, the glycosylation sites of the glycoproteins were predicted with the NetNGlyc 1.0 and NetOGlyc 3.1 programs. The detected proteins were predicted to be about 90% of the total proteins identified by matching an NXS/T sequence for N-linked glycosylation and an S/T sequence for O-linked, glycosylation (Table 3). Thus, it could be seen that more than about 90% of the identified proteins contained one or more glycosylation sites. A reproducibility of about 71.4% and an efficiency of glyprotein concentration of 90% in protein detection show that the profiling of serum glycoprotein-linked LC-MS/NIS is very useful for the discovery of serum biomarkers.

TABLE 3

Proteins identified by LC-MS/MS analysis, number of glycosylated proteins and glycosylation sites

| Samples | Protein ID | Proteins containing N-linked glycosylation sites | Proteins containing O-linked glycosylation sites | Total glyco-proteins | Percentage of glycoproteins |
|---|---|---|---|---|---|
| Normal sample | 132 | 97 | 89 | 119 | 90.2% |
| Cancer sample | 148 | 106 | 101 | 133 | 89.9% |

<3-3> Comparison of Expression of Glycoproteins in Cancer Samples and Normal Samples The glycoproteins identified in cancer samples were analyzed comparatively with the glycoproteins identified in normal samples. 99 proteins were commonly detected in the sera of three cancer patients, and among them, 38 proteins were expressed highly in the sera of cancer patients compared to those in normal persons. Meanwhile, some of glycoproteins identified in the normal serum 2 (N2) were different from the other normal sera with respect to MS scores and the number of hit peptides. Thus, the N2 data were excluded. It was shown that the number of the hit peptides of the 38 proteins were about 1.5-fold higher than that in normal persons. In particular, the number of hit peptides of 21 proteins among the cancer glycoproteins was two-fold higher than that of the normal glycoproteins (Table 4). About 60% of the 38 proteins belong to proteins which are not highly expressed in human serum. Also, it was reported to some of these proteins can be used as lung cancer markers in the sera or plasmas of lung cancer patients. Examples thereof include heptoglobin (HP), inter-alpha-trypsin inhibitor H4 (ITI-H4), complement C3 precursor, and leucin-rich alpha 2 glycoprotein. Proteins other than these proteins are not yet known as lung cancer markers or biomarkers.

The 38 proteins, which increased in the sera of lung cancer patients, consisted of 6 IGgs (15.8%), 8 high abundant protein (21.1%), 1 hemoglobulin (2.6%) and 23 non-high abundant proteins (60.5%). Such results indicate that the concentration and isolation of serum proteins are useful tools for the identification of low abundant proteins.

TABLE 4

Lung cancer biomarkers identified by the present invention

| | | Scores | | Peptides (hit) | | |
|---|---|---|---|---|---|---|
| IPN No. | Protein names | Cancer | Normal | Cancer | Normal | Fold |
| IPI00294395.1 | Complement component c8 beta chain precursor | 17 | 0.0 | 4 | 0.0 | — |
| IPI00027462.1 | Protein s100-a9 | 17 | 0.0 | 3 | 0.0 | — |
| IPI00021727.1 | C4b-binding protein alpha chain precursor | 40 | 13.3 | 15 | 2.7 | 5.75 |
| IPI00186903.3 | Isoform 2 of apolipoprotein-II precursor | 23 | 3.3 | 4 | 0.7 | 5.50 |
| IPI00007047.1 | Protein s100-a8 | 20 | 6.7 | 6 | 1.3 | 4.50 |
| IPI00250430 | Similar to cavia porcellus phosphatidic acid phosphatase 2A mRNA | 10 | 3.3 | 3 | 0.7 | 4.50 |
| IPI00022395.1 | Complement component c9 precursor | 43 | 26.7 | 21 | 5.0 | 4.20 |
| IPI00028413.4 | Inter-alpha-trypsin inhibitor heavy chain h3 precursor | 17 | 3.3 | 3 | 0.7 | 4.00 |
| IPI00168728.1 | FIj00385 protein (fragment) | 60 | 20.0 | 28 | 7.7 | 3.65 |
| IPI00019581.1 | Coagulation factor xii precursor | 13 | 3.3 | 4 | 1.3 | 3.00 |
| IPI00384948.3 | Ig alpha-2 chain c region | 10 | 6.7 | 5 | 1.7 | 3.00 |
| IPI00011252.1 | Complement component c8 alpha chain precursor | 10 | 6.7 | 5 | 1.7 | 2.80 |
| IPI00027482.1 | Corticosteriod-binding globulin precursor | 23 | 6.7 | 4 | 1.7 | 2.60 |
| IPI00291262.3 | Clusterin precursor | 47 | 56.7 | 36 | 14.0 | 2.60 |
| IPI00030809 | Gamma-g globin | 13 | 6.7 | 17 | 7.0 | 2.48 |
| IPI00022391.1 | Serum amyloid p-component precursor | 33 | 16.7 | 11 | 4.7 | 2.36 |
| IPI00008558.1 | Plasma kallikrein precursor | 40 | 26.7 | 13 | 5.7 | 2.29 |
| IPI00166866.3 | Ighal protein | 23 | 16.7 | 13 | 6.7 | 2.00 |
| IPI00292950.4 | Heparin cofactor 2 precursor | 27 | 16.7 | 7 | 3.3 | 2.00 |
| IPI00334432.3 | 16 kDa protein | 33 | 10.0 | 12 | 6.0 | 2.00 |
| IPI00385252.1 | Ig kappa chain v-iii region gol | 10 | 3.3 | 3 | 1.3 | 2.00 |
| IPI00291867.3 | Complement factor I precursor | 57 | 50.0 | 16 | 8.3 | 1.92 |
| IPI00382950.1 | Hemoglobin subunit beta | 40 | 23.3 | 41 | 22.0 | 1.88 |
| IPI00164623.3 | Complement 3 precursor fragment | 293 | 116.7 | 142 | 77.7 | 1.83 |
| IPI00431645 | Hp protein | 130 | 110.0 | 529 | 291.0 | 1.82 |
| IPI00060731.5 | Similar to tripartite motif protein 49 | 10 | 6.7 | 3 | 1.7 | 1.80 |
| IPI00019591.1 | Isoform 1 of complement b precursor (fragment) | 53 | 36.7 | 37 | 21.0 | 1.78 |
| IPI00553177.1 | Alpha-1-antitrypsin precursor | 93 | 86.7 | 211 | 119.9 | 1.76 |
| IPI00218192.1 | Isoform 2 of inter-alpha-trypsin inhibitor heavy chain h4 precursor | 143 | 92.7 | 91 | 51.7 | 1.75 |

TABLE 4-continued

Lung cancer biomarkers identified by the present invention

| IPN No. | Protein names | Scores Cancer | Scores Normal | Peptides (hit) Cancer | Peptides (hit) Normal | Fold |
|---|---|---|---|---|---|---|
| IPI00022417.4 | Leucine-rich alpha-2-glycoprotein precursor | 27 | 10.0 | 7 | 4.0 | 1.75 |
| IPI00479116.1 | Carboxypeptidase n subunit precursor | 20 | 6.7 | 4 | 2.3 | 1.71 |
| IPI00027507.1 | Complement factor h-related protein 3 precursor | 20 | 16.7 | 3 | 2.0 | 1.67 |
| IPI00291866.4 | Plasma protease C1 inhibitor precursor | 113 | 86.7 | 145 | 87.0 | 1.67 |
| IPI00550315.1 | Ig kappa chain c region | 10 | 10.0 | 25 | 15.0 | 1.67 |
| IPI00550315.2 | Alpha 2 macroglobulin variant | 213 | 126.7 | 173 | 106.3 | 1.63 |
| IPI00027547.2 | Dermcidin precursor | 13 | 6.7 | 4 | 2.3 | 1.57 |
| IPI0003229.1 | Complement c5 precursor | 63 | 40.0 | 10 | 6.7 | 1.55 |
| IPI00025426.1 | Pregnancy zone protein precursor | 40 | 26.7 | 59 | 39.3 | 1.51 |

The 38 selected proteins shown in Table 4 were classified, according to intracellular distribution, into extracellular proteins and membrane proteins (FIG. 3A). Also, such proteins were classified according to molecular functions (FIG. 3B) and biological processes (FIG. 3). In a viewpoint of molecular functions, 20% of the 38 proteins had endopeptidase inhibitory activity, 15% had antigen binding activity, and 11% had trypsin activity. In a viewpoint of biological processes, most of the 38 proteins were associated with transport and immune-inflammatory response proteins.

Example 4

Western Blotting of Inter-Alpha-Trypsin Inhibitor Heavy Chain h3 Precursor

Whether Inter-alpha-trypsin inhibitor heavy chain h3 precursor (ITI-H3) among the 38 proteins selected in Example 3 is specifically expressed only in the sera of lung cancer patients was analyzed by Western blotting.

20 μg of the serum glycoproteins, obtained from each of the cancer patients and the normal persons in Example 2, were loaded onto 15% SDS-PAGE. After electrophoresis, the gel was transferred to a nitrocellulose membrane (Whatman, Germany). The proteins were diluted with monoclonal goat anti-ITI-H3 antibody (Santa cruz, Calif., USA) at 1:500 dilution and incubated at 4° C. overnight. Then, the proteins were diluted with anti-goat IgG antibody (Santa cruz, Calif., USA) at 1:2,000 dilution and incubated at room temperature for 1 hour. To detect signals, the ECL advanced Western blotting system was used.

Figure 4:
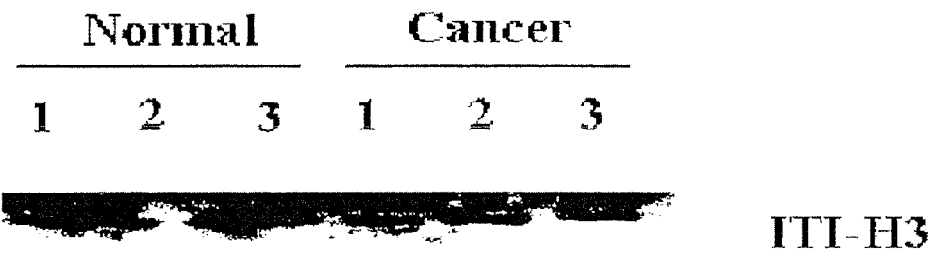
FIG. 4 shows the results of Western blotting of inter-alpha trypsin inhibitor H3 in lung cancer patients and normal persons.

In the experimental results, in the LC-MS/MS analysis of the normal sera, ITI-H3 was not identified, but in the Western blotting, it was detected even in the normal sera. However, it was shown that ITI-H3 was expressed highly in the lung cancer sera compared to the normal sera (FIG. 4A). Accordingly, it can be seen that ITI-H3 can be used as a biomarker for lung cancer.

Example 5

Analysis of Peptide Number of Plasma Kallikrein

Peptides of plasma kallikrein (KLKB1) were detected from 3 normal persons (N1, N2 and N3) and 3 lung cancer patients (C1, C2 and C3) using a mass spectrometer. In the experimental results, it could be seen that the number of the peptides detected in the lung cancer patients was larger than in the normal persons. Particularly, the peptide number of the H4 domain was about 3-fold larger in the cancer patients than in the normal persons (Table 5).

TABLE 5

Peptide number of plasma kallikrein

| | N1 | N2 | N3 | C1 | C2 | C3 |
|---|---|---|---|---|---|---|
| H1 | 0 | 6 | 2 | 5 | 8 | 3 |
| H3 | 0 | 1 | 0 | 1 | 0 | 0 |
| H4 | 0 | 2 | 2 | 3 | 6 | 3 |
| L | 0 | 8 | 0 | 2 | 9 | 0 |

H1, H3 and H4: heavy chain domains
L: light chain domain

Example 6

Western Blotting 1 of Plasma Kallikrein Fragment

On the basis of the results of Example 5, whether the H4 domain of KLKB1 is specifically expressed only in the sera of lung cancer patients was analyzed by Western blotting using an epitope antibody.

The sera, obtain from the lung cancer patients (C1, C2 and C3), or the glycoproteins, obtained from the sera using the lectin column, were concentrated, and then analyzed by Western blotting. 100 of each concentrate of the sera or 20 μg of each of the glycoproteins was loaded onto 15% SDS-PAGE. After electrophoresis, the gel was transferred to a nitrocellulose membrane (Whatman, Germany). The sera were diluted with anti-KLKB1 antibody (Santa Cruz, prepared using an epitope of amino acid residues 361-400 of plasma kallikrein) at 1:1,200 dilution and incubated at 4° C. overnight. Then, the sera were diluted with anti-goat IgG antibody (Santa cruz, Calif., USA) at 1:2,000 dilution and incubated at room temperature for 1 hour.

To detect signals, the ECL advanced Western blotting analysis system (Amersham Biosciences, UK) was used. In the results of Western blot of the concentrated glycoproteins, a band having a size of 15-20 kDa was detected only in the samples of lung cancer patients at high levels. Also, in the experimental results obtained using the sera, a band of 15-20 kDa was detected in the sera of lung cancer patients at a level higher than in the normal persons (FIG. 5).

Example 7

Western Blotting 2 of Plasma Kallikrein Fragment

100 µl of each of the whole sera of normal persons or lung cancer patients 50-60 years old was loaded onto 15% SDS-PAGE, and then subjected to Western blot in the same manner as in Example 6.

The sera were treated with anti-KLKB1 antibody (1:200 dilution) and incubated at 4° C. overnight, followed by incubation at room temperature for 1 hour. In the experimental results, a KLKB1 fragment of 18 kDa was detected in 13 patients of the 14 lung cancer patients. However, it was not substantially detected in the normal persons (FIG. 6).

Example 8

Western Blotting 3 of Plasma Kallikrein Fragment

The whole sera of normal persons or lung cancer patients more than 65-year-old were collected, and whether KLKB1 is specifically expressed only in the sera of the lung cancer patients was analyzed by Western blotting in the same manner as in Example 7.

In the experimental results, a KLKB1 of 18 kDa was detected in 12 patients of the 14 lung cancer patients at high levels. However, it was weakly detected in only one person of the normal persons (FIG. 7).

Example 9

Western Blotting 4 of Plasma Kallikrein Fragment

The whole sera of 34 normal persons and 24 lung cancer patients 50-70 years old were additionally collected, and whether the KLKB1 fragment is specifically expressed in the sera of the lung cancer patients was analyzed by Western blot in the same manner as in Example 7.

In the experimental results, in the normal persons, the KLKB1 fragment was not substantially detected or was detected at low levels, but in the lung cancer patients, the KLKB1 fragment was detected in 20 of the 24 patients at high levels (see FIGS. 9 to 12).

In Examples 7 to 9, a total of 42 normal persons and 52 patients were subjected to Western blot and, as a result, it could be seen that the 18 kDa fragment was weakly detected in 17 persons of the 42 normal persons, very weakly detected in 11 persons and was not detected in 14 persons, and it was detected in 45 patients of the 52 lung cancer patients at high levels. From these results, it could be seen that the 18 kDa fragment was detected in 45 of the 52 lung cancer patients, and thus it had a sensitivity of 87% and a specificity of 67%. Meanwhile, the level of the 18 kDa fragment in the normal persons was lower than that in the lung cancer patients.

INDUSTRIAL APPLICABILITY

As described above, the inventive diagnostic markers for lung cancer are specifically expressed only in the sera of lung cancer patients at high levels, and thus will be very useful for diagnosing lung cancer and estimating disease progression and treatment.

---

The invention claimed is:

1. A method for diagnosing lung cancer in a subject, the method comprising:
   (i) isolating and concentrating glycoproteins from a biological sample of the subject by using a multi-lectin affinity column packed with ConA (concanavalinA), LCH (lentil lectin), GNA (snowdrop lectin), WGA (wheat germ agglutinin), SNA (elderberry lectin), MAL (*Maackia amurensis* lectin), AIL (Jacalin), and PNA (peanut agglutinin);
   (ii) denaturing the isolated and concentrated glycoproteins in a buffer containing mercaptoethanol and octyl beta-D-glucopyranoside;
   (iii) deglycosylating the denatured glycoproteins in a reaction buffer comprising peptide-N-glycosidase F (PNGase F);
   (iv) separating the deglycosylated glycoproteins using sodium dodecyl sulfate polyacrylamide gel electrophoresis (SDS-PAGE);
   (v) transferring the SDS-PAGE separated glycoproteins onto a Western blot membrane;
   (vi) treating the Western blot membrane containing the transferred glycoproteins with a primary antibody and a secondary antibody to form an antigen-antibody complex wherein the glycoproteins from the biological sample comprise a plasma kallikrein fragment (KLKB1) which comprises SEQ. ID NO: 1 and is present on the Western blot membrane,
      wherein the primary antibody is an anti-KLKB1 antibody that binds an epitope within amino acid residues of 361-400 of the plasma kallikrein fragment, and the secondary antibody binds the primary antibody; and
   (vii) diagnosing lung cancer in the subject when a 15-20 kDa mass fragment band on the Western blot membrane which corresponds to the plasma kallikrein fragment is detected at a level higher than a normal level found in a healthy person.

2. The method of claim 1, wherein the secondary antibody comprises an anti-goat IgG antibody.

3. The method of claim 1, wherein the ConA, LCH and GNA in the multi-lectin affinity column capture N-glycosylated proteins.

4. The method of claim 1, wherein the WGA, SNA and MAL in the multi-lectin affinity bind to sialic acid modified proteins.

5. The method of claim 1, wherein the 15-20 kDa mass fragment comprises an 18 kDa mass fragment.

6. The method of claim 1, wherein the Western blot membrane comprises nitrocellulose.

7. The method of claim 1, wherein detecting the formation of the antigen-antibody complex that corresponds to the 15-20 kDa mass fragment band is performed by using quantitative or qualitative measurement techniques which uses at least one selected from the group consisting of enzymes, fluorescent substances, ligands, luminescent substances, microparticles, redox molecules and radioactive isotopes.

8. The method of claim 7, wherein
   the enzymes are selected from the group consisting of β-glucuronidase, β-D-glucosidase, β-D-galactosidase, urease, peroxidase, alkaline phosphatase, acetylcholine esterase, glucose oxidase, hexokinase, malate dehydrogenase, glucose-6-phosphate dehydrogenase, and invertase;
   the fluorescent substances are selected from the group consisting of fluorescein, isothiocyanate, rhodamine, phycoerythrin, phycocyanin, allophycocyanin, fluorescein, and isothiocyanate;
   the luminescent substances are selected from the group consisting of acridinium ester, luciferin, and luciferase acrydinium ester;
   the microparticles are selected from the group consisting of colloidal gold and colored latex;
   the redox molecules are selected from the group consisting of ruthenium complexes, viologen, quinone, Ti ions, Cs ions, diimide, 1,4-benzoquinone, and hydroquinone; and
   the radioactive isotopes are selected from the group consisting of $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

9. The method of claim 1, wherein the biological sample is selected from the group consisting of whole blood, plasma and serum.

10. The method of claim 1, wherein the biological sample comprises serum.

11. A method for diagnosing lung cancer in a subject, the method comprising:
   (i) isolating and concentrating glycoproteins from plasma of the subject by using a multi-lectin affinity column packed with ConA (concanavalinA), LCH (lentil lectin), GNA (snowdrop lectin), WGA (wheat germ agglutinin), SNA (elderberry lectin), MAL (*Maackia amurensis* lectin), AIL (Jacalin), and PNA (peanut agglutinin);
   (ii) denaturing the isolated and concentrated glycoproteins in a buffer containing mercaptoethanol and octyl beta-D-glucopyranoside at about 100° C. for about 10 minutes;
   (iii) deglycosylating the denatured glycoproteins in a reaction buffer comprising peptide-N-glycosidase F (PNGase F);
   (iv) separating the deglycosylated glycoproteins using a 15% sodium dodecyl sulfate polyacrylamide gel electrophoresis (15% SDS-PAGE);
   (v) transferring the 15% SDS-PAGE separated glycoproteins onto a Western blot nitrocellulose membrane;
   (vi) treating the Western blot membrane containing the transferred glycoproteins with a primary antibody and a secondary antibody to form an antigen-antibody complex wherein the glycoproteins from the biological sample comprise a plasma kallikrein fragment (KLKB1) which comprises SEQ. ID NO: 1 and is present on the Western blot membrane,
wherein the primary antibody is an anti-KLKB1 antibody that binds an epitope within amino acid residues of 361-400 of the plasma kallikrein fragment, and
the secondary antibody binds to the primary antibody; and
(vii) diagnosing lung cancer in the subject when a 15-20 kDa mass fragment band on the Western blot membrane which corresponds to the plasma kallikrein fragment is detected at a level higher than a normal level found in a healthy person.

* * * * *